United States Patent
Cheng et al.

(10) Patent No.: US 7,327,949 B1
(45) Date of Patent: Feb. 5, 2008

(54) HEATER ASSEMBLY FOR A RESPIRATORY TREATMENT MACHINE

(75) Inventors: Yao-Ming Cheng, Tu-Cheng (TW); Kung-Kuan Lai, Tu-Cheng (TW); Chun-Wei Huang, Tu-Cheng (TW)

(73) Assignee: Apex Medical Corp., Taipei Hsien (TW)

( * ) Notice: Subject to any disclaimer, the term of this patent is extended or adjusted under 35 U.S.C. 154(b) by 0 days.

(21) Appl. No.: 11/645,914

(22) Filed: Dec. 27, 2006

(51) Int. Cl.
*F24H 1/18* (2006.01)

(52) U.S. Cl. ............... 392/444; 392/441; 392/459; 219/443.1; 128/203.12; 128/204.17

(58) Field of Classification Search ............... None
See application file for complete search history.

(56) References Cited

U.S. PATENT DOCUMENTS 5,558,084 A * 9/1996 Daniell et al. ......... 128/203.17
5,640,951 A * 6/1997 Huddart et al. ......... 128/204.17
7,111,624 B2 * 9/2006 Thudor et al. ......... 128/203.16

* cited by examiner

*Primary Examiner*—Thor S. Campbell
(74) *Attorney, Agent, or Firm*—Alan Kamrath; Kamrath & Associates PA (57) ABSTRACT

A heating assembly for a respiratory treatment machine includes a base and a water tank. The base has a receiving space communicating with a recessed platform at a via an opening, and a heating plate securely placed on a bottom face of the receiving space. The water tank has a main receptacle, a secondary receptacle integrally formed and communicating with the main receptacle and movably received inside the receiving space, a conducting plate securely provided at a bottom face of the main receptacle and an extension integrally formed with the conducting plate and provided at a bottom face of the secondary receptacle. The extension has a dimension corresponding to that of the heating plate such that after the secondary receptacle is received inside the receiving space, the extension is placed on top of the heating plate and engaged with the heating plate.

19 Claims, 8 Drawing Sheets

HEATER ASSEMBLY FOR A RESPIRATORY TREATMENT MACHINE

BACKGROUND OF THE INVENTION

1. Field of the Invention

The present invention relates to a heater assembly, and more particularly to a heater assembly for a respiratory treatment machine.

2. Description of the Prior Art

Figure 7:
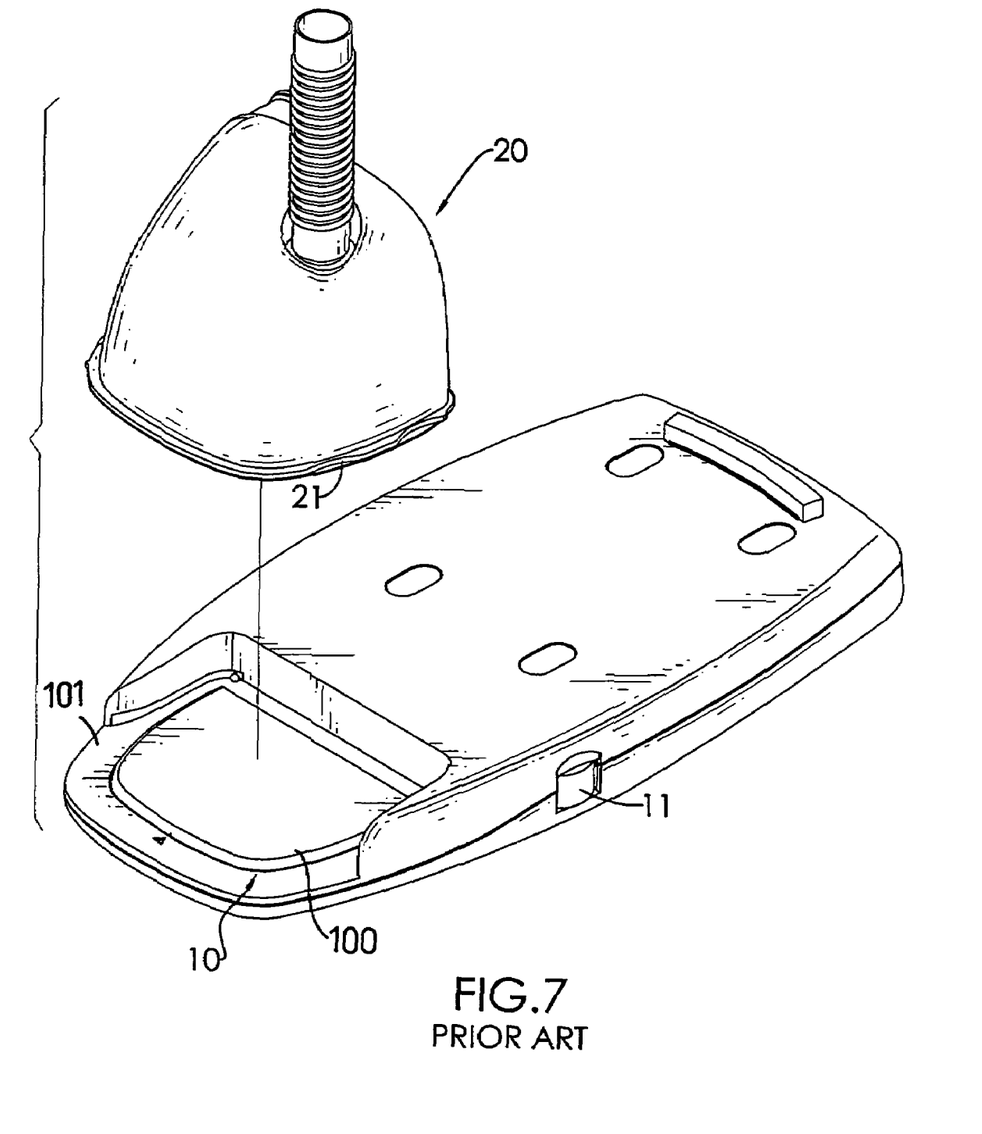
FIG. 7 is an exploded perspective view of a conventional heating assembly.
Figure 8:
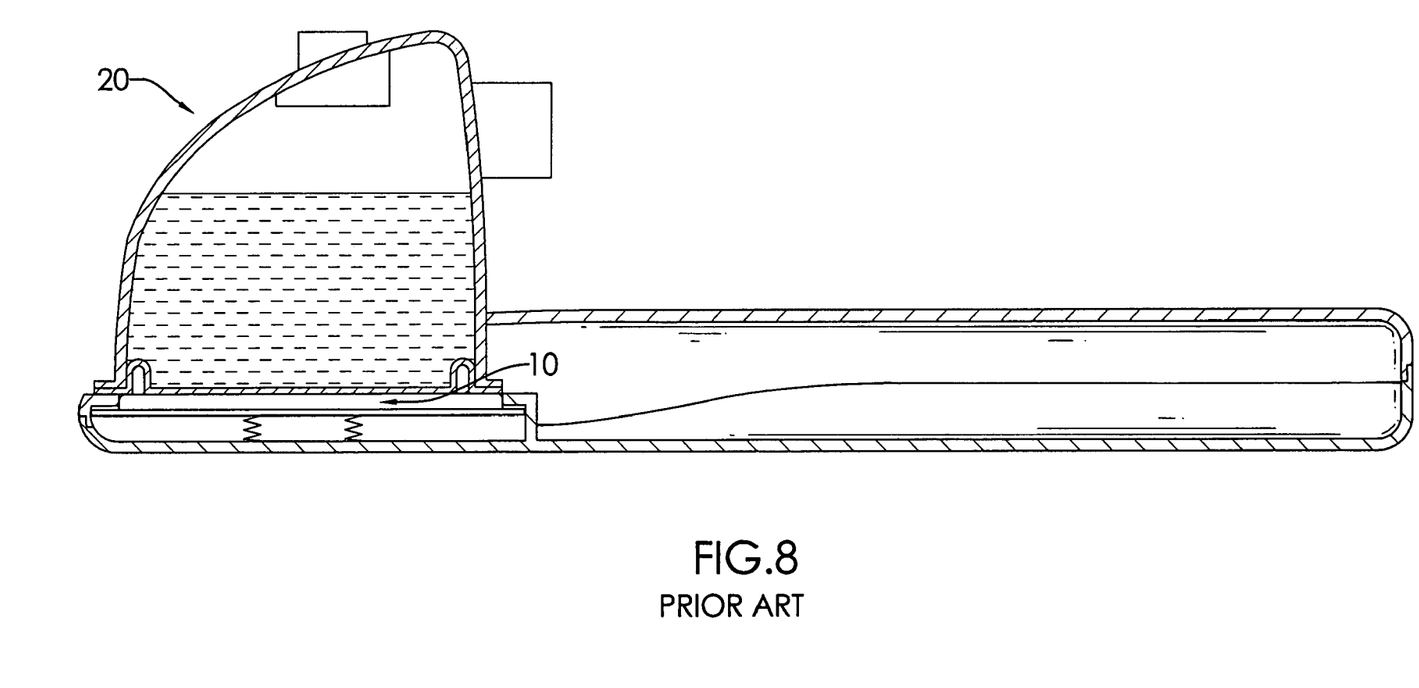
FIG. 8 is a schematic cross sectional view showing that the conventional water tank and the base are combined.

A respiratory treatment machine, as shown in FIGS. 7 and 8, includes a base (10) and a water tank (20). The base (10) has a heating plate (100) mounted on a side face of a recessed platform (101) which is defined in a front side of the base (10). A controlling knob (11) is provided on a side of the base (10). The water tank (20) has a heat conducting plate (21) formed at a bottom side of the water tank (20) and corresponding to the heating plate (100). The water tank (20) is designed to receive therein water such that after the water tank (20) is placed on top of the heating plate (100) and the controlling knob (11) is turned on, temperature of the heating plate (100) gradually turns the water inside the water tank (20) into vapor. Then the user is able to use a hose to suck in the vapor to treat respiratory problems.

From the depiction of the drawings, it is noted that the heating plate (100) is exposed to the air and there is nothing to protect the user from engagement with the heating plate (100). Therefore, if the controlling knob (11) is accidentally turned on and the temperature of the heating plate (100) starts to rise, the user may be easily hurt by the high temperature of the heating plate (100). Even after the heating process is finished and the controlling knob (11) is not turned off, the user may still easily be hurt by the temperature of the heating plate (100).

To overcome the shortcomings, the present invention tends to provide an improved heating assembly to mitigate the aforementioned problems.

SUMMARY OF THE INVENTION

The primary objective of the present invention is to provide a heating assembly for a respiratory treatment machine. The heating assembly of the present invention has a heating plate and a protection gate to guard the heating plate from engagement by the user such that the user is protected.

In order to accomplish the objective of the present invention, the heating assembly of the present invention has a base and a water tank. The base is provided with a recessed platform, a receiving space defined inside the base and communicating with the platform via an opening of the receiving space and a heating plate placed on a bottom face of the receiving space. A protection gate is pivotally mounted at a side face of the opening of the receiving space. The water tank is provided with a secondary receptacle extending outward from and communicating with the water tank. A conducting plate is provided at a bottom face of the water tank and an extension integrally formed with the conducting plate is provided at a bottom face of the secondary receptacle. Therefore, after the secondary receptacle is received in the receiving space, the engagement between the heating plate and the extension of the water tank allows the temperature of the heating plate to be conducted to the extension as well as the conducting plate such that the water inside the water tank is heated. The provision of the protection gate prevents accidental touch to the heating plate such that the user is protected.

Another objective of the present invention is that multiple springs are provided between the heating plate and a bottom face of the receiving space so that after the secondary receptacle is pushed into the receiving space, the heating plate is depressed by the secondary receptacle and the engagement therebetween is secured.

Still another objective of the present invention is that a magnet is provided at a side face of the secondary receptacle and a magnetic switch is provided at a side face of the receiving space such that only after the magnetic switch senses the existence of the magnetic force from the magnet, can the magnetic switch be activated.

Other objects, advantages and novel features of the invention will become more apparent from the following detailed description when taken in conjunction with the accompanying drawings.

DETAILED DESCRIPTION OF THE PREFERRED EMBODIMENT

Figure 1:
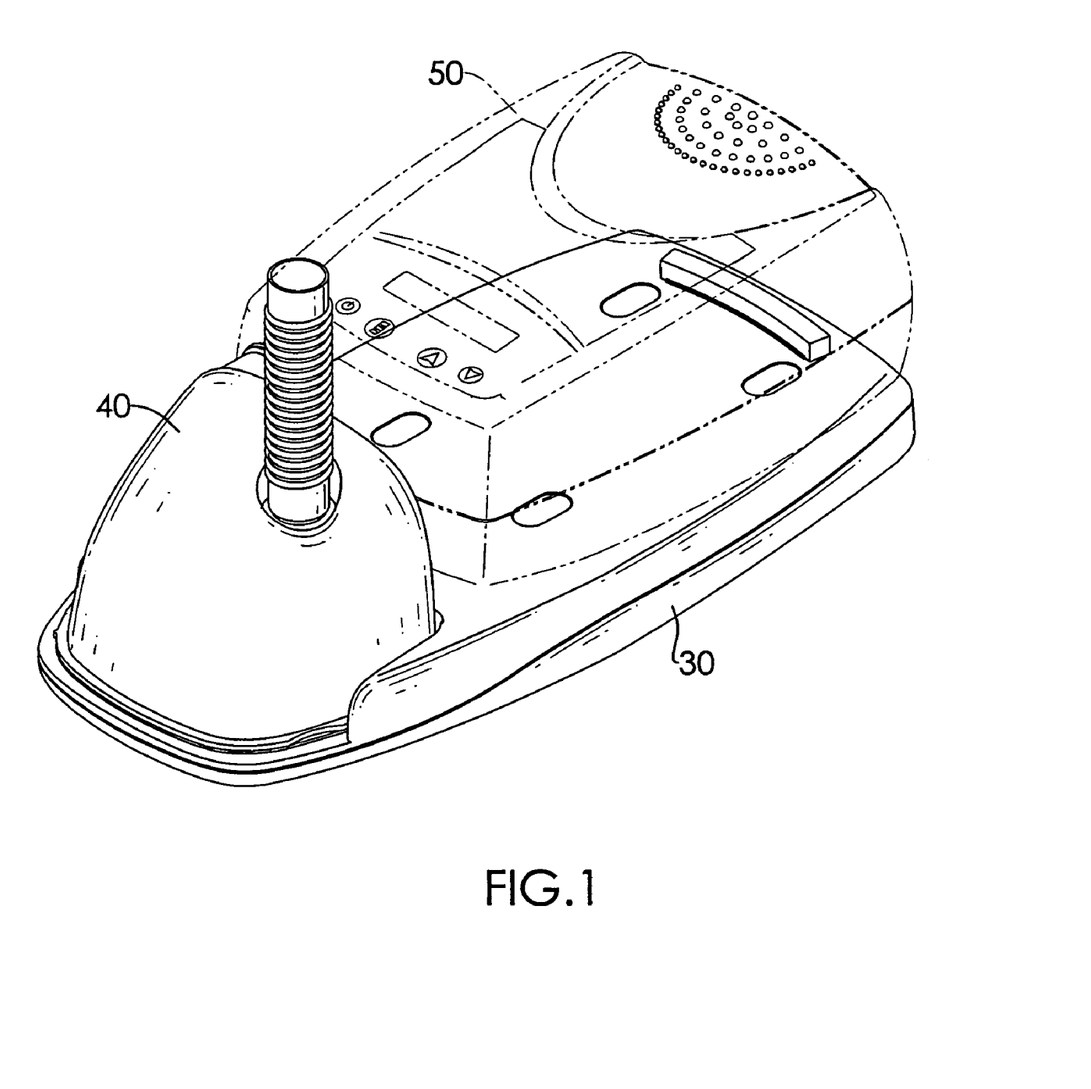
FIG. 1 is a perspective view of the respiratory treatment machine and the heating assembly of the present invention.

With reference to FIG. 1, it is noted that the heating assembly in accordance with the present invention normally is associated with a respiratory treatment machine (50). However, because the respiratory treatment machine (50) is not the focus of the present invention, the function and the structure thereof is omitted for clarity and brevity. It is noted that the heating assembly of the present invention is composed of a base (30) and a water tank (40).

Figure 2:
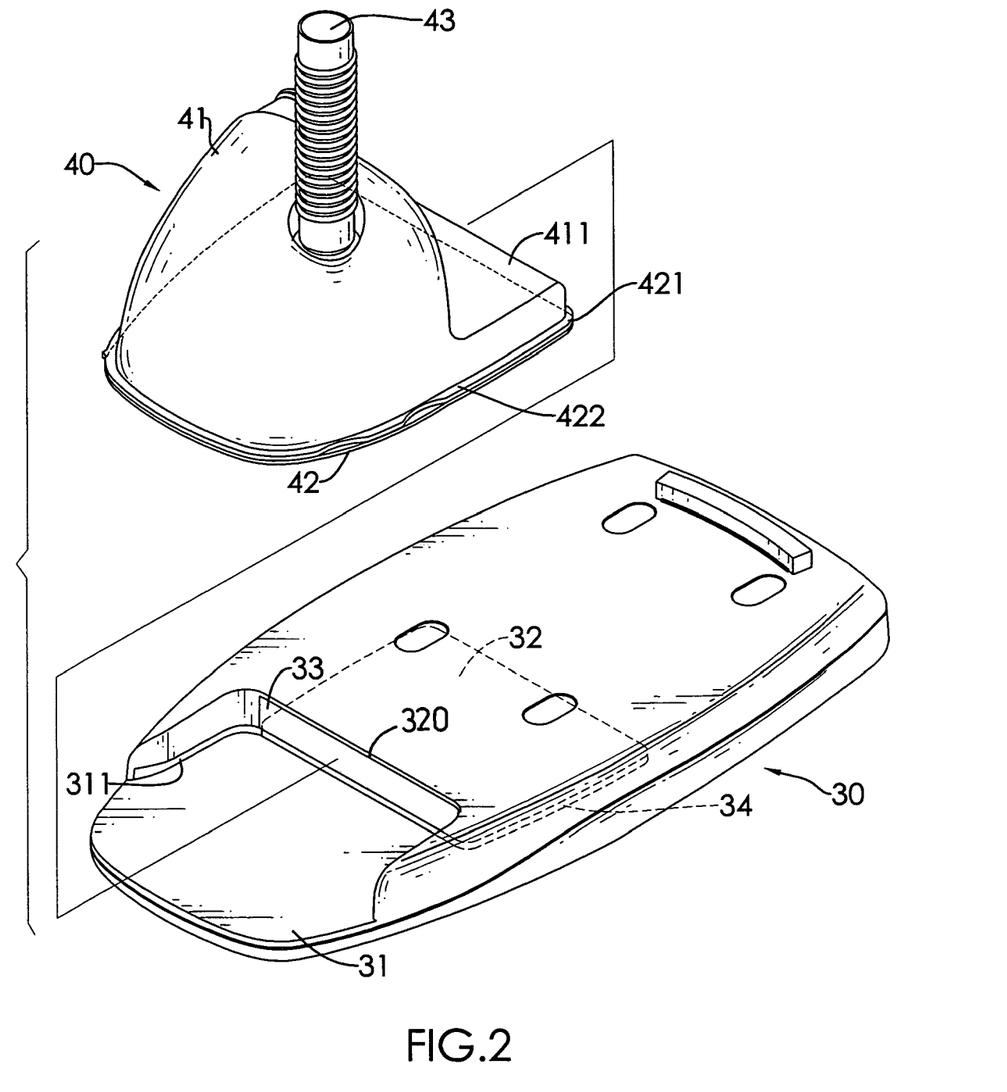
FIG. 2 is an exploded perspective view of the heating assembly of the present invention.

With reference to FIG. 2, the base (30) includes a recessed platform (31) formed at a front side of the base (30), a receiving space (32) defined inside the base (30) to communicate with the platform (31) via an opening (320), a protection gate (33) pivotally mounted at a side face defining the opening (320) and a heating plate (34) securely placed on a bottom face of the receiving space (32). A guiding track (311) is defined in two opposite sides of the platform (31).

The water tank (40) has a main receptacle (41) and a conducting plate (42) placed at a bottom face of the main receptacle (41). A vapor tube (43) is extending out of the main receptacle (41) and communicates with the main receptacle (41). In addition to the main receptacle (41), a secondary receptacle (411) is extending out from a side of the main receptacle (41) and communicates with the main receptacle (41). Also, an extension (421) is integrally formed with the conducting plate (42) and mounted at a bottom face of the secondary receptacle (411). It is noted that a guiding rail (422) is formed on two opposite sides of the secondary receptacle (411) to correspond to and be received in the guiding track (311) of the base (30).

Figure 3:
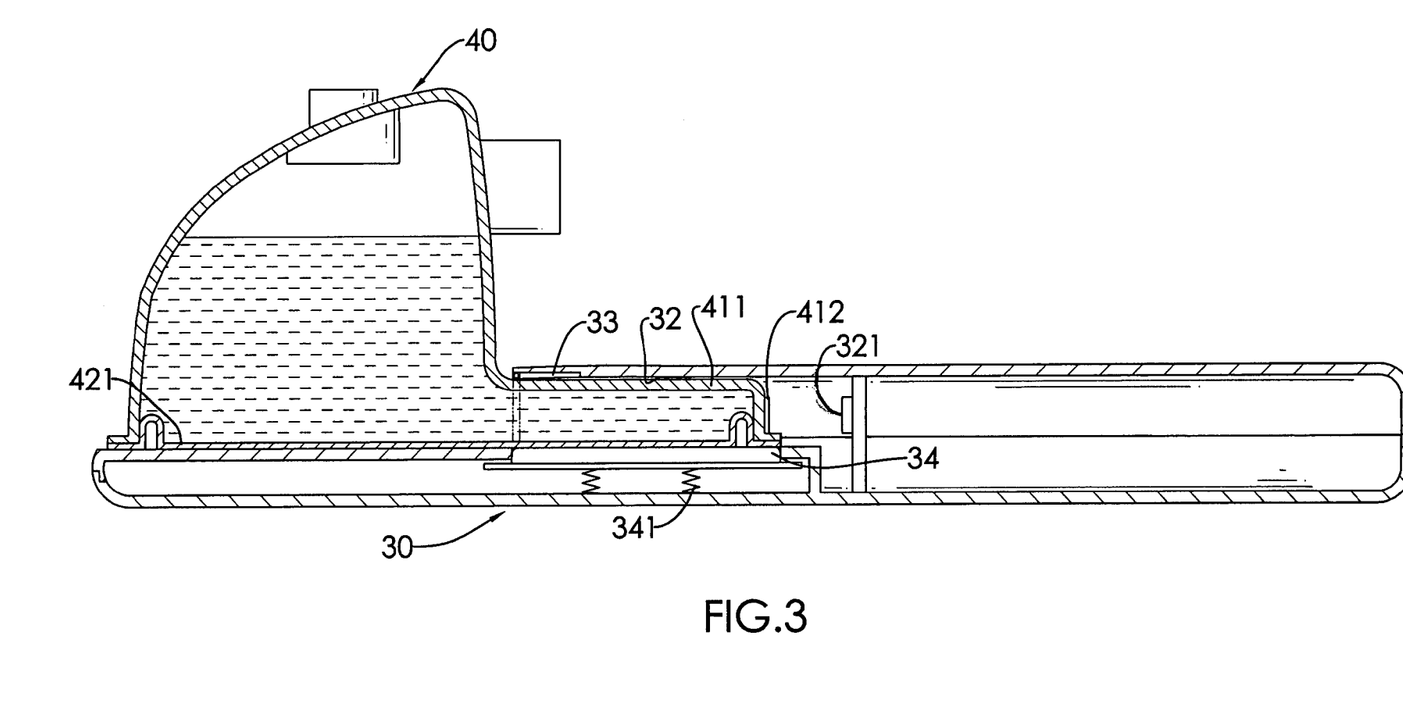
FIG. 3 is a cross sectional view showing the combination of the heating assembly.

With reference to FIGS. 2 and 3, it is to be noted that when the base (30) and the water tank (40) are combined, the guiding rail (422) at two opposed sides of the secondary receptacle (411) is first received in the corresponding guiding track (311) of the base (30). Then while the water tank (40) is pushed forward toward the receiving space (32), the protection gate (33) is forced to pivot and the opening (320) is opened to allow extension of the secondary receptacle (411) as well as the extension (421). The movement of the water tank (40) is stopped when a side face of the main receptacle (41) engages with a side face of the opening (320). At the time when the movement of the water tank (40) is stopped by the base (30), the extension (421) is perfectly on top of the heating plate (34) such that the temperature of the heating plate (34) is able to be gradually conducted to the extension (421) as well as the conducting plate (42). As a result, the water inside the main receptacle (41) as well as in the secondary receptacle (411) is heated for turning into vapor.

It is noted that because the heating plate (34) is concealed inside the receiving space (32) and the protection gate (33) is provided at the opening (320) of the receiving space (32), even after the heating process is finished, the temperature of the heating plate (34) will not hurt the user. Further, in order to secure the engagement between the extension (421) and the heating plate (34), multiple springs (341) are provided between the heating plate (34) and the bottom face of the receiving space (32) such that when the extension (421) is extended into the receiving space (32), the heating plate (34) is pressed downward inside the receiving space (32) and that the engagement between the extension (421) and the heating plate (34) is secured.

Figure 4:
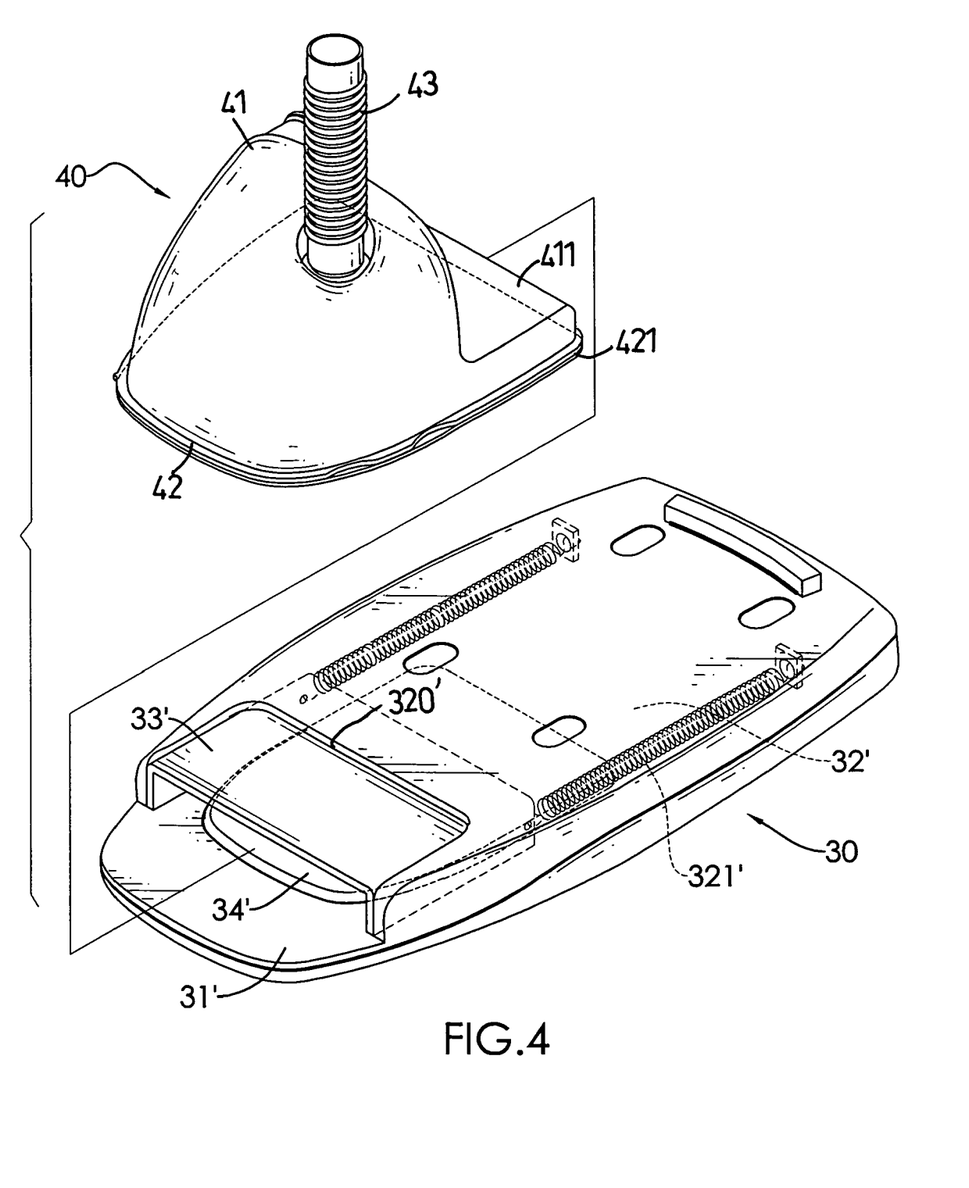
FIG. 4 is an exploded perspective view of the heating assembly in a different embodiment.

With reference to FIG. 4, it is noted that in this embodiment, the heating assembly of the present invention also includes a water tank (40) and a base (30').

The water tank (40) has a main receptacle (41) and a conducting plate (42) placed at a bottom face of the main receptacle (41). A vapor tube (43) is extending out of the main receptacle (41) and communicates with the main receptacle (41). In addition to the main receptacle (41), a secondary receptacle (411) is extending out from a side of the main receptacle (41) and communicates with the main receptacle (41). Also, an extension (421) is integrally formed with the conducting plate (42) and mounted at a bottom face of the secondary receptacle (411). The base (30') includes a recessed platform (31') formed at a front side of the base (30'), a receiving space (32') defined inside the base (30') to communicate with the platform (31') via an opening (320'), a protection gate (33') movably mounted at a side face defining the opening (320') and a heating plate (34') securely placed on a bottom face of the receiving space (32').

From the depiction of the accompanying drawing, it is noted that the heating plate (34') extends out of the receiving space (32) in the first embodiment so that the heating plate (34') has a dimension equal to the sum of the conducting plate (42) and the extension (421). A protection gate (33') is mounted at the opening (320') and has two compressible springs (321') respectively mounted at two opposed sides of the protection gate (33'). Two free ends of the two compressible springs (321') are respectively and securely mounted to a side face of the receiving space (32').

Figure 5:
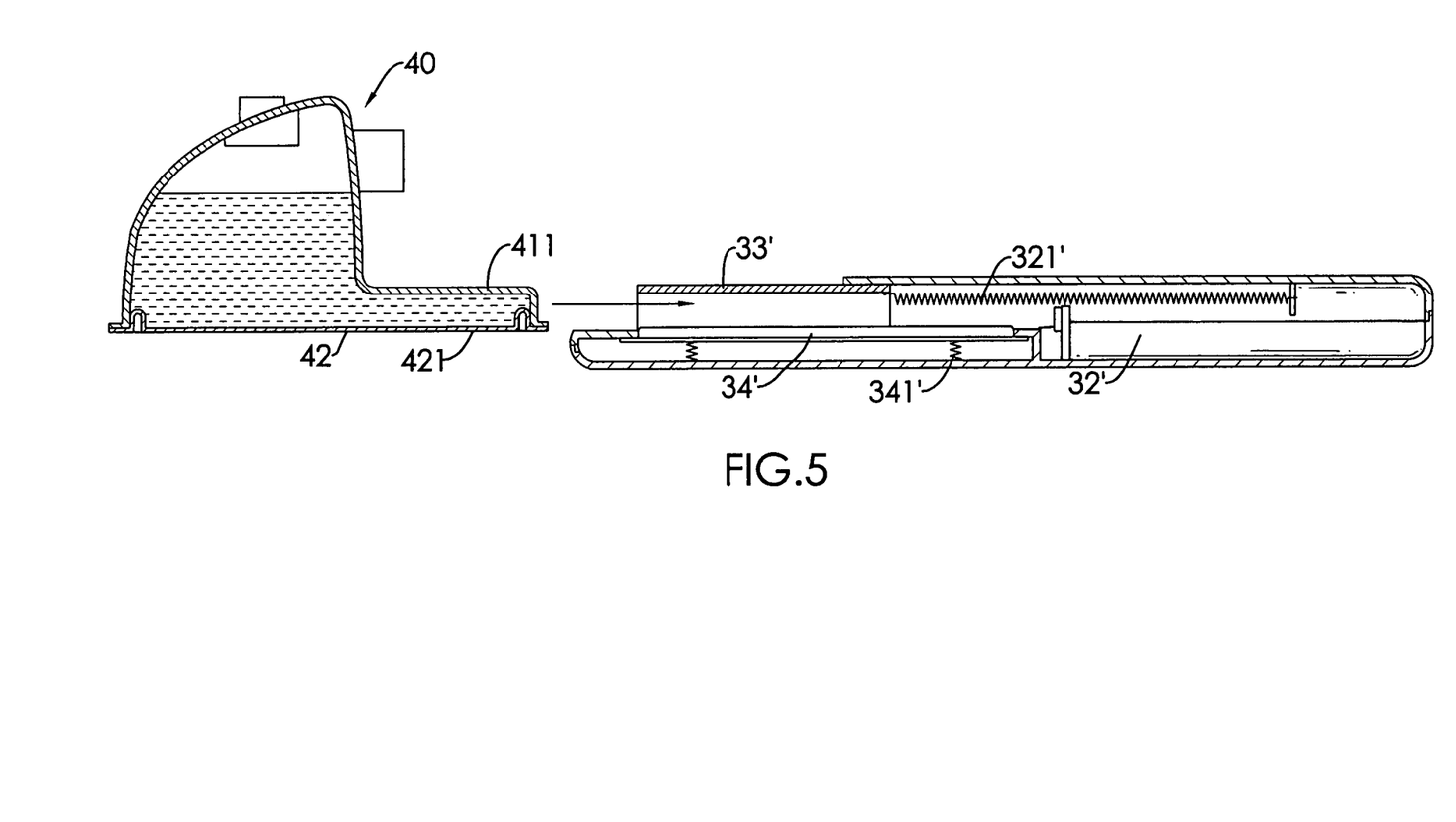
FIG. 5 is a cross sectional view showing that the water tank is to be combined with the base.
Figure 6:
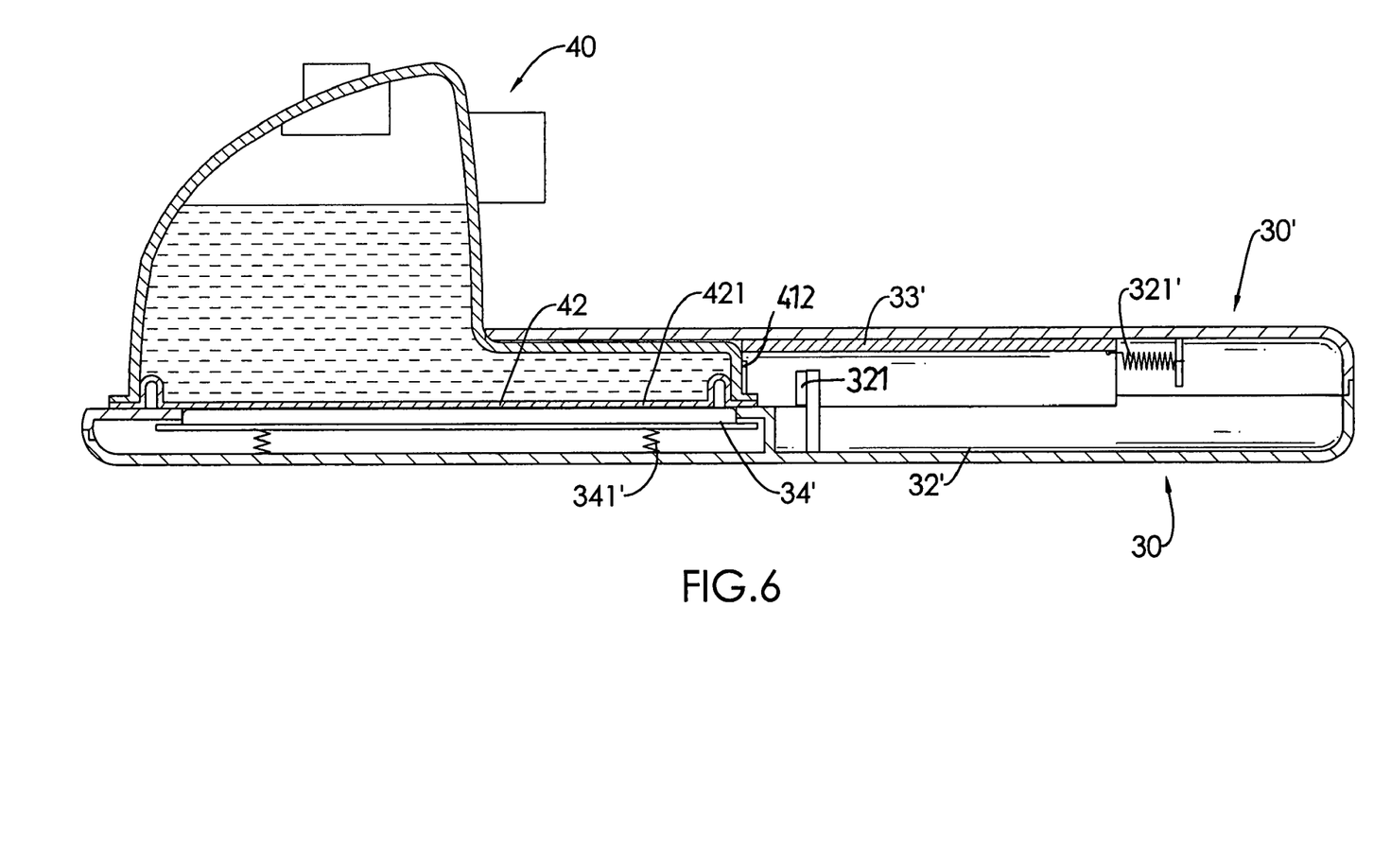
FIG. 6 is a cross sectional view showing the combination of the heat assembly in the embodiment as shown in FIG. 4.

With reference to FIGS. 5 and 6, when the water tank (40) is to be combined with the base (30'), the secondary receptacle (411) is first aligned with the receiving space (32'). Then the secondary receptacle (411) is moved forward to push open the protection gate (33'). The compressible springs (321') are compressed while the protection gate (33') is pushed into the receiving space (32') and the springs (341') sandwiched between the heating plate (34') and a bottom face of the receiving space (32) are also compressed while the heating plate (34') is forced to move toward the bottom face of the receiving space (32') via the secondary receptacle (411). After the conducting plate (42) and the extension (421) are perfectly aligned with the heating plate (34'), the heating assembly is ready for heating the water inside the water tank (40).

Referring to FIG. 3 and taking FIG. 2 for reference, it is noted that a magnet (412) is provided at a side face of the secondary receptacle (411) and a magnetic switch (321) is provided at a side face of the receiving space (32, 32'). When the water tank (40) is moved close to the side face of the receiving space (32,32'), the magnetic switch (321) senses the magnetic force of the magnet (412) such that the magnetic switch (321) is automatically turned on to provide electricity to active the heating plate (34,34'). After the heating process is finished and the water tank (40) is removed from the receiving space (32,32'), the magnetic switch (321) automatically turns off the provision of electricity to the heating plate (34,34'). Therefore, the safety of the user is protected due to the automatic power turning on/off mechanism. Also, the protection gate (33,33') provides protection the user in that the protection gate (33,33') prevent the user from engagement to the heating plate (34,34').

It is to be understood, however, that even though numerous characteristics and advantages of the present invention have been set forth in the foregoing description, together with details of the structure and function of the invention, the disclosure is illustrative only, and changes may be made in detail, especially in matters of shape, size, and arrangement of parts within the principles of the invention to the full extent indicated by the broad general meaning of the terms in which the appended claims are expressed.

What is claimed is:

1. In a heating assembly for a respiratory treatment machine, the heating assembly comprising a base and a water tank, wherein the improvement comprises:

the base has a receiving space defined inside the base and communicating with a recessed platform at a front side of the base via an opening, and a heating plate securely placed on a bottom face of the receiving space, the water tank has a main receptacle, a secondary receptacle integrally formed and communicating with the main receptacle and movably received inside the receiving space, a conducting plate securely provided at a bottom face of the main receptacle and an extension integrally formed with the conducting plate and provided at a bottom face of the secondary receptacle, the extension has a dimension corresponding to that of the heating plate such that after the secondary receptacle is received inside the receiving space, the extension is placed on top of the heating plate and engaged with the heating plate.

2. The heating assembly as claimed in claim 1, wherein a protection gate is movably provided at the opening of the receiving space to selectively cover the opening.

3. The heating assembly as claimed in claim 2, wherein a magnet is provided at a side face of the secondary receptacle and a magnetic switch is provided at a side face of the receiving space such that interaction between the magnet and the magnetic switch controls activation of the heating plate.

4. The heating assembly as claimed in claim 1, wherein a pair of guiding tracks are formed on two opposed sides of the platform and a pair of guiding rails are formed on two opposed side of the secondary receptacle so that the guiding rails are correspondingly received inside the guiding tracks when the secondary receptacle is to be received inside the receiving space.

5. The heating assembly as claimed in claim 2, wherein a pair of guiding tracks are formed on two opposed sides of the platform and a pair of guiding rails are formed on two opposed side of the secondary receptacle so that the guiding rails are correspondingly received inside the guiding tracks when the secondary receptacle is to be received inside the receiving space.

6. The heating assembly as claimed in claim 3, wherein a pair of guiding tracks are formed on two opposed sides of the platform and a pair of guiding rails are formed on two opposed side of the secondary receptacle so that the guiding rails are correspondingly received inside the guiding tracks when the secondary receptacle is to be received inside the receiving space.

7. The heating assembly as claimed in claim 6, wherein springs are provided between the heating plate and the bottom face of the receiving space to secure engagement between the heating plate and the extension when the extension is on top of the heating plate.

8. A heating assembly for a respiratory treatment machine, the heating assembly having a base and a water tank, wherein the improvement comprises:
the base has a receiving space defined inside the base and communicating with a recessed platform at a front side of the base via an opening, a heating plate securely placed on a bottom face of the receiving space and means for controlling activation of the heating plate,
the water tank has a main receptacle, a secondary receptacle integrally formed and communicating with the main receptacle and movably received inside the receiving space, a conducting plate securely provided at a bottom face of the main receptacle and an extension integrally formed with the conducting plate and provided at a bottom face of the secondary receptacle, the extension has a dimension corresponding to that of the heating plate such that after the secondary receptacle is received inside the receiving space, the extension is placed on top of the heating plate and engaged with the heating plate.

9. The heating assembly as claimed in claim 8, wherein a protection gate is movably provided at the opening of the receiving space to selectively cover the opening.

10. The heating assembly as claimed in claim 9, wherein the activation means is composed of a magnet provided at a side face of the secondary receptacle and a magnetic switch provided at a side face of the receiving space such that interaction between the magnet and the magnetic switch controls activation of the heating plate.

11. The heating assembly as claimed in claim 8, wherein a pair of guiding tracks are formed on two opposed sides of the platform and a pair of guiding rails are formed on two opposed side of the secondary receptacle so that the guiding rails are correspondingly received inside the guiding tracks when the secondary receptacle is to be received inside the receiving space.

12. The heating assembly as claimed in claim 9, wherein a pair of guiding tracks are formed on two opposed sides of the platform and a pair of guiding rails are formed on two opposed side of the secondary receptacle so that the guiding rails are correspondingly received inside the guiding tracks when the secondary receptacle is to be received inside the receiving space.

13. The heating assembly as claimed in claim 10, wherein a pair of guiding tracks are formed on two opposed sides of the platform and a pair of guiding rails are formed on two opposed side of the secondary receptacle so that the guiding rails are correspondingly received inside the guiding tracks when the secondary receptacle is to be received inside the receiving space.

14. The heating assembly as claimed in claim 11, wherein springs are provided between the heating plate and the bottom face of the receiving space to secure engagement between the heating plate and the extension when the extension is on top of the heating plate.

15. A heating assembly for a respiratory treatment machine, the heating assembly having a base and a water tank, wherein the improvement comprises:
the base has a receiving space defined inside the base and communicating with a recessed platform at a front side of the base via an opening, a heating plate securely placed on a bottom face of both the platform and the receiving space and means for controlling activation of the heating plate,
the water tank has a main receptacle, a secondary receptacle integrally formed and communicating with the main receptacle and movably received inside the receiving space, a conducting plate securely provided at a bottom face of the main receptacle and an extension integrally formed with the conducting plate and provided at a bottom face of the secondary receptacle, combination of the extension and the conducting plate has a dimension corresponding to that of the heating plate such that after the secondary receptacle is received inside the receiving space, the conducting plate and the extension are placed on top of the heating plate and engaged with the heating plate.

16. The heating assembly as claimed in claim 15, wherein a protection gate is movably provided at the opening of the receiving space to selectively cover the opening.

17. The heating assembly as claimed in claim 15, wherein the activation means is composed of a magnet provided at a side face of the secondary receptacle and a magnetic switch provided at a side face of the receiving space such that interaction between the magnet and the magnetic switch controls activation of the heating plate.

18. The heating assembly as claimed in claim 16, wherein the activation means is composed of a magnet provided at a side face of the secondary receptacle and a magnetic switch provided at a side face of the receiving space such that interaction between the magnet and the magnetic switch controls activation of the heating plate.

19. The heating assembly as claimed in claim 18, wherein a pair of guiding tracks are formed on two opposed sides of the platform and a pair of guiding rails are formed on two opposed side of the secondary receptacle so that the guiding rails are correspondingly received inside the guiding tracks when the secondary receptacle is to be received inside the receiving space.

* * * * *